United States Patent
Cortese et al.

(10) Patent No.: US 10,773,048 B2
(45) Date of Patent: Sep. 15, 2020

(54) METHODS AND COMPOSITIONS FOR HUMIDIFICATION AND COOLING OF GAS STREAMS

(71) Applicant: Cool Vapor Solutions, Arroyo Grande, CA (US)

(72) Inventors: Dean R. Cortese, Salinas, CA (US); William E. Beecher, Jr., Arroyo Grande, CA (US)

(73) Assignee: Cool Vapor Solutions, Salinas, CA (US)

(*) Notice: Subject to any disclaimer, the term of this patent is extended or adjusted under 35 U.S.C. 154(b) by 0 days.

(21) Appl. No.: 16/660,394

(22) Filed: Oct. 22, 2019

(65) Prior Publication Data

US 2020/0046932 A1 Feb. 13, 2020

Related U.S. Application Data

(63) Continuation of application No. PCT/US2019/017730, filed on Feb. 12, 2019.

(60) Provisional application No. 62/630,030, filed on Feb. 13, 2018, provisional application No. 62/789,436, filed on Jan. 7, 2019.

(51) Int. Cl.
| | | |
|---|---|---|
| *A61M 16/16* | (2006.01) | |
| *A61M 16/10* | (2006.01) | |
| *A61M 16/08* | (2006.01) | |

(52) U.S. Cl.
CPC .......... *A61M 16/16* (2013.01); *A61M 16/109* (2014.02); *A61M 16/0875* (2013.01); *A61M 16/101* (2014.02); *A61M 16/107* (2014.02)

(58) Field of Classification Search
CPC ............ A61M 16/101; A61M 16/0816; A61M 16/0875; A61M 16/1075; A61M 16/1085; A61M 16/109; A61M 16/107; A61M 16/16; A61M 39/10; F24F 6/04; F25D 3/00; F25D 2303/082; F25D 2317/0413; H01M 8/04171
See application file for complete search history.

(56) References Cited

U.S. PATENT DOCUMENTS

| | | | |
|---|---|---|---|
| 4,606,866 A | 8/1986 | McGlothlin et al. | |
| 5,062,420 A * | 11/1991 | Levine .................. | A61M 16/08 128/204.18 |
| 5,176,415 A * | 1/1993 | Choksi .................. | A61M 39/10 128/202.27 |

(Continued)

FOREIGN PATENT DOCUMENTS

| | | |
|---|---|---|
| WO | 00/55225 A1 | 9/2000 |
| WO | 2012/077159 A1 | 6/2012 |

(Continued)

OTHER PUBLICATIONS

Essential Humidity for a successful noninvasive ventilation strategy, 2015, Fisher & Paykel Healthcare, www.fphcare.com.

*Primary Examiner* — Kathryn E Ditmer
(74) *Attorney, Agent, or Firm* — FisherBroyles, LLP; Jill A. Jacobson

(57) ABSTRACT

Methods and systems are provided for humidification of gas streams, such as air or oxygen. Hydrated superabsorbent polymers are used to provide humidity to flowing gas streams. Humidified gas streams may be used in respiratory therapy and other applications for which humidified air is desired and/or beneficial.

23 Claims, 10 Drawing Sheets

(56) References Cited

U.S. PATENT DOCUMENTS

| | | | |
|---|---|---|---|
| 5,536,258 A * | 7/1996 | Folden | A61M 39/16 604/265 |
| 6,332,462 B1 * | 12/2001 | Krohn | A61M 16/1075 128/204.15 |
| 7,478,760 B2 | 1/2009 | Beatty et al. | |
| 7,815,127 B2 | 10/2010 | Beatty et al. | |
| 7,927,655 B2 | 4/2011 | Lee | |
| RE43,865 E | 12/2012 | Faust et al. | |
| 9,114,381 B2 | 8/2015 | Lee et al. | |
| 9,884,785 B2 | 2/2018 | Liguori | |
| 2002/0076533 A1 * | 6/2002 | Caceres | A41D 20/005 428/195.1 |
| 2003/0033829 A1 * | 2/2003 | Smith | A62B 9/003 62/480 |
| 2004/0202703 A1 * | 10/2004 | Meyer-Ingold | A01N 59/16 424/445 |
| 2006/0037613 A1 * | 2/2006 | Kwok | A61M 16/16 128/203.27 |
| 2006/0144399 A1 | 7/2006 | Davidowski et al. | |
| 2006/0254305 A1 * | 11/2006 | Urfig | F24F 5/0017 62/425 |
| 2008/0051674 A1 * | 2/2008 | Davenport | A61B 5/087 600/561 |
| 2008/0190427 A1 * | 8/2008 | Payton | A61M 16/0666 128/203.27 |
| 2009/0056716 A1 * | 3/2009 | Carrier | A61M 15/00 128/204.15 |
| 2009/0114553 A1 | 5/2009 | Hultz | |
| 2012/0091218 A1 | 4/2012 | Mikkelsen et al. | |
| 2014/0338669 A1 * | 11/2014 | Zhao | A61M 16/0816 128/204.18 |
| 2015/0250331 A1 * | 9/2015 | Thorman | F25D 7/00 221/1 |
| 2015/0292797 A1 * | 10/2015 | Fan | F25D 31/00 62/64 |
| 2017/0035985 A1 * | 2/2017 | Newland | A61M 16/024 |
| 2017/0106333 A1 | 4/2017 | Zhu | |
| 2018/0221618 A1 | 8/2018 | Strauss et al. | |

FOREIGN PATENT DOCUMENTS

| | | | | |
|---|---|---|---|---|
| WO | WO-2015136489 A1 * | 9/2015 | | A61M 16/066 |
| WO | 2019/160833 A1 | 8/2019 | | |

\* cited by examiner

MINI END CAP-C2 BACK VIEW

MINI END CAP-C2 FRONT VIEW

MINI PISTON - P1 BACK VIEW

MINI PISTON - P1 FRONT VIEW

MINI PISTON - P2 BACK VIEW

MINI PISTON - P2 FRONT VIEW

MINI PERFORATED TUBE SCREEN

MINI PERFORATED TUBE END

SERVICE CAP PORT PLUG

MAX V2 TOP CAP-C2 SIDE VIEW

MAX V2-TP1 PERFORATED TOP PLATE

MAX V2 BOTTOM CAP-C3 SIDE TOP VIEW

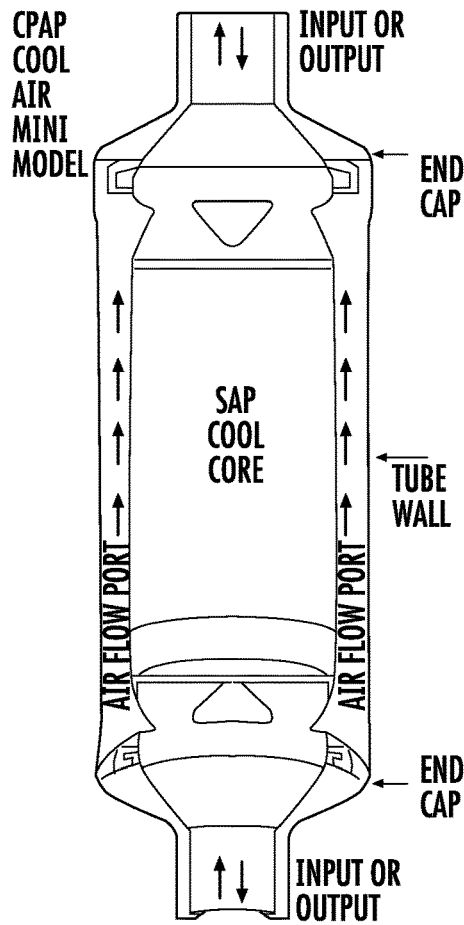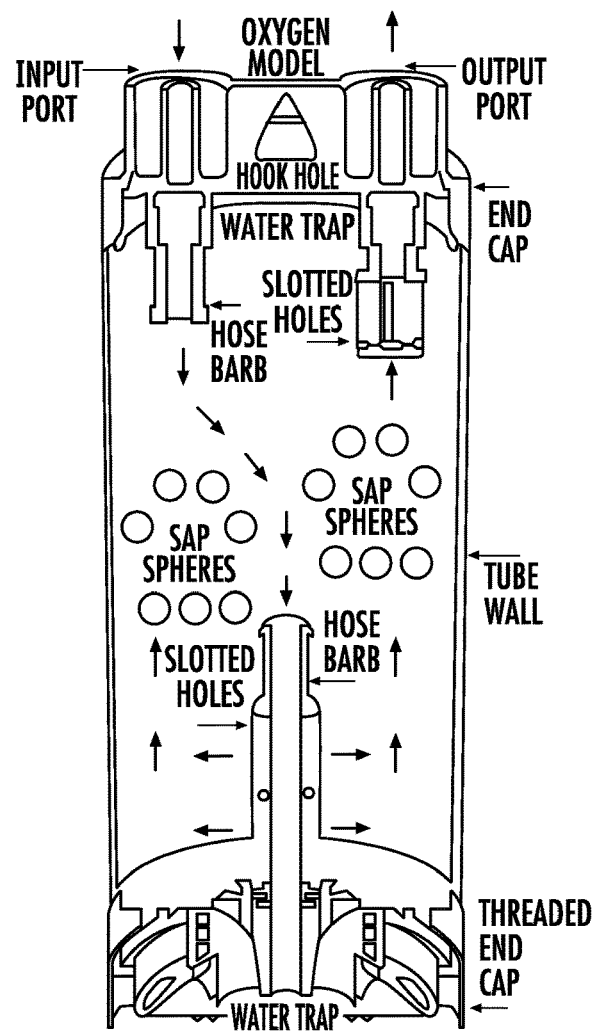
FIG. 31                          FIG. 32
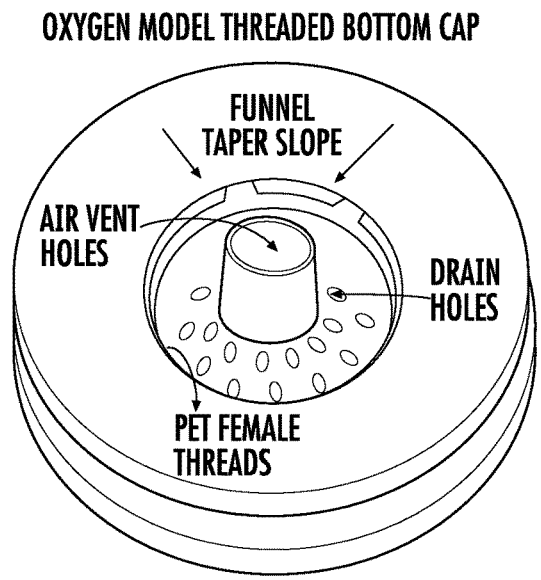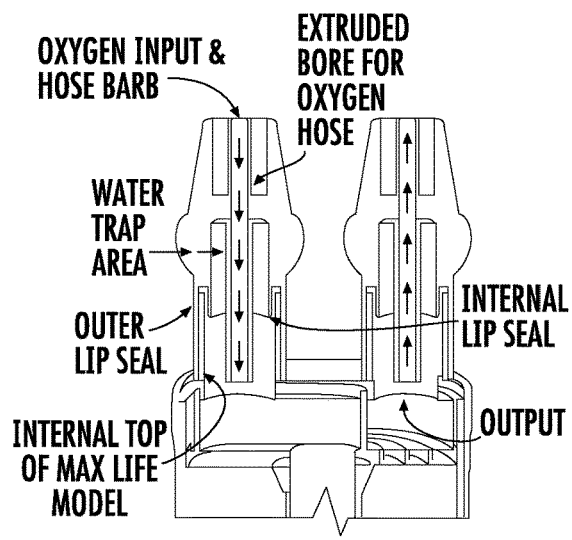
FIG. 33                          FIG. 34

METHODS AND COMPOSITIONS FOR HUMIDIFICATION AND COOLING OF GAS STREAMS

CROSS-REFERENCE TO RELATED APPLICATIONS

This application is a continuation of PCT/US2019/017730, filed on Feb. 12, 2019, which claims the benefit of U.S. Provisional Application No. 62/630,030, filed on Feb. 13, 2018, and U.S. Provisional Application No. 62/789,436, filed on Jan. 7, 2019, both of which are incorporated herein by reference in their entireties.

FIELD OF THE INVENTION

The invention relates to polymeric compositions and methods of use thereof for humidification and cooling of gas streams, particularly for therapeutic uses.

BACKGROUND

Humidification has become a standard of care for Continuous Positive Airway Pressure (CPAP) therapy for sleep apnea, and for oxygen therapy, which is used for various lung disease treatment processes. Breathing normally, the air is warmed, filtered and humidified while going through a patient's nose before the air passes to the lower airways. The airway lumen is lined by epithelial cells with many hair-like cilia that transport mucus and foreign particles out of the lungs. The removal of moisture from the airways can cause the mucus to become dry and sticky, inhibiting the removal of particles. A study has shown that breathing dry air for only 30 minutes can cause the mucociliary transport to slow down due to water loss. (https://www.fphcare.co.nz/files/documents/hospital/therapy-overview-brochures/niv-humidification-therapy-review-niv_en_185042174/) Inadequate humidification may cause distress to CPAP and oxygen patients and may have serious consequences. These deficiencies can result in drying the oral and nasal airways, causing a sore, dry and inflamed throat and an increase in airway resistance and also result in increased rhinitis/rhinorrhea and nasal congestion. Thickened secretions reduce mucociliary clearance in extreme cases, resulting in the formation of a mass of secretions, which can occlude the airway. Increased bronchoconstriction further restricts the flow of gas to the lungs and increases the work of breathing (WOB).

Sleep apnea, if left untreated, increases the risk for a number of conditions, including high blood pressure, heart attack, stroke, obesity, diabetes, heart failure, arrhythmia, and work-related or driving accidents. CPAP includes the use of positive airway pressure applied through the nasal airway to alleviate obstructed breathing passageways during sleep.

A drawback with commercially available CPAP devices is that the flowing air tends to dry out the patient's nasal mucosa, thus reducing compliance. A number of solutions have been attempted. Passive humidification has been used, in which the high pressure air passes over cool water, but this increases humidity only by a small amount. Heated humidifiers have also been used, in which a heating pad is placed under a water tub, thus producing water vapor which may be picked up by the pressurized air stream. This increases relative humidity from the initial level of about 45-50% to an improved level of about 60-80%, and this has consequently improved CPAP compliance.

CPAP machines have become smaller and quieter over the years, but an undesirable byproduct of these advancements has been an increase in heat buildup, which manifests as rainout/condensation buildup in the non-heated tubing through which the pressurized air transits. Heated tubing has been implemented to increase the temperature of the outer diameter of the tube, to insulate the heated humidified air traveling through, thereby preventing condensation. However, although condensation is prevented, the relative humidity of the air stream is lower than with use of a heated humidifier as described above. The heated tube dries out the air, usually dropping the Relative Humidity by as much as 10-30%, contributing to patient discomfort and decreasing compliance with CPAP therapy. There are estimated more than 22 million CPAP users in the U.S. and more than 100 million worldwide, and even with the heated humidifier technology available today, it is estimated that 50% to 70% still complain of nasal and oral dryness.

There is a need for an improved method to humidify high pressure gas streams such as air or oxygen for use in therapeutic methods.

BRIEF SUMMARY OF THE INVENTION

Methods and systems are provided herein for humidifying and in some embodiments, purifying a gas stream such as air or oxygen. Methods of treatment for conditions, such as respiratory conditions, in which humidified air is therapeutically beneficial, are also provided.

In one aspect, methods are provided for humidifying a flowing gas stream, such as air or oxygen. The methods include flowing an input gas stream, e.g., air or oxygen, over a hydrated superabsorbent polymer (SAP). Water from the hydrated SAP enters the input gas stream. After the input gas stream picks up water from the hydrate SAP, it becomes an output gas stream, which is humidified. The hydrated SAP captures heat from the input gas stream, thereby cooling the gas stream, and the humidified output gas stream is consequently a lower temperature than the input gas stream. Over time, the hydrated SAP becomes less hydrated as water vapor is transferred to the flowing gas stream. In some embodiments, the hydrated SAP continues to humidify the gas stream at a suitable level until the SAP reaches a hydration level of about 25% of the capacity of the polymer to absorb water.

In some embodiments, the pressure at which the input gas stream flows over the hydrated SAP is about 1 cmH2O to about 30 cmH2O.

In some embodiments, the input gas stream, e.g., air or oxygen, is at ambient temperature, such as about 68° F. to about 88° F. In some embodiments, the input gas stream may have a relative humidity of about 1% to about 68%.

In some embodiments, the humidified output gas stream is at a temperature of about 60° F. to about 80° F.

In some embodiments, the humidified output gas stream has a relative humidity of about 85% to about 99%. In some embodiments, the output gas stream has a relative humidity that is about 20% to about 90% higher than the input gas stream. In one embodiment, in the context of a CPAP device, the relative humidity of the output air stream (e.g., air) may be about 20% to about 45% higher relative humidity than the input air stream. In another embodiment, in the context of an oxygen concentrator, the output oxygen stream may be about 80% to about 90% higher relative humidity than the input oxygen stream. In one embodiment, in the context of an oxygen concentrator running with a bubble humidifier, the output oxygen stream is about 5% to about 15% higher relative humidity than the input oxygen stream.

In some embodiments, the humidified output gas stream is up to about 12° F. cooler than the input gas stream. In one embodiment, in the context of a CPAP device, the output air stream may be up to about 6° F. to about 12° F. cooler than the input air stream, depending on ambient conditions. In another embodiment, in the context of an oxygen concentrator, the output oxygen stream may be 0° F. to about 8° F. cooler than the input oxygen stream, depending on ambient conditions.

In some embodiments, the SAP that is utilized in the methods and systems described herein includes 2-propenoic acid. For example, the SAP may be sodium polylacrylate or acrylamide/potassium acrylate copolymer. In some embodiments, the SAP is crosslinked. For example, the SAP may be crosslinked with sodium 2-propenoate.

In some embodiments, the SAP is in the form of spherical or substantially spherical units. For example, each spherical unit may include a diameter of about of about 1.0 mm to about 3.0 mm dry to about 5 mm to about 13 mm hydrated.

In some embodiments, the SAP includes an antimicrobial substance, for example, ionic silver, absorbed therein.

In some embodiments, the hydrated SAP is retained in a housing through which the input gas stream flows.

In another aspect, methods are provided for humidification of air delivered through a continuous positive airway pressure (CPAP) device. The methods include any of the methods described above for humidifying a flowing gas stream, wherein the input gas stream is air and wherein the humidified output gas stream is humidified air, and wherein the humidified air is delivered through tubing to an individual in need thereof, e.g., an individual suffering from sleep apnea. In some embodiments, the tubing of the CPAP device is not heated from an external heating source. In some embodiments, the pressure of the humidified output air stream that is delivered to the individual is about 1 cmH2O to about 30 cmH2O.

In another aspect, methods are provided for humidification of oxygen delivered through an oxygen tank. The methods include any of the methods described above for humidifying a flowing gas stream, wherein the input gas stream is oxygen, e.g., from an oxygen tank, and wherein the humidified output gas stream is humidified oxygen, and wherein the humidified oxygen is delivered through tubing to an individual in need thereof, e.g., an individual suffering from a condition for which supplemental oxygen is therapeutically beneficial. In some embodiments, the flow rate of the humidified output oxygen stream that is delivered to the individual is about 0.5 Lpm to about 15 Lpm.

In another aspect, methods are provided for humidification of air in an environment, such as a room or a building or a humidifier device. The methods include any of the methods described above for humidifying a flowing gas stream, wherein the input gas stream is air from the environment and wherein the output gas stream is humidified air.

In some embodiments, the humidified output air stream is released to the environment. In other embodiments, the humidified output air stream is delivered to an individual in need of humidified air, e.g., through tubing.

In another aspect, methods are provided for humidifying and purifying air in an environment, such as a room or a building or a humidifier/air purification device. The input gas stream may be air from the environment that includes substance(s) to be removed, for example, such as contaminants and/or particulate matter, e.g., for the benefit of individuals breathing the air. The air is filtered prior to or after contact with the hydrated SAP, and wherein the humidified output gas stream includes a reduced amount of the substance(s) to be removed, such as contaminants and/or particulate matter, in comparison with the input air stream.

In some embodiments, the humidified and purified output air stream is released to the environment. In other embodiments, the humidified and purified output air stream is delivered to an individual in need of humidified air, e.g., through tubing.

In some embodiments, the hydrated SAP is retained in an air purification system. For example, the air purification system may include a filter, such as a high efficiency particulate air (HEPA) filter.

In some embodiments, the air from the environment includes pollen, and wherein the output gas stream comprises a reduced amount of pollen in comparison with the input gas stream.

In some embodiments of the methods herein, the gas stream is further routed through a device that includes a cooling core, wherein the cooling core comprises a frozen material, and wherein the gas stream in contact with the cooling core cools, thereby providing an output gas stream that is a lower temperature than the output gas stream in the absence of the device with the cooling core, e.g., the output gas stream from contact with SAP alone.

In another aspect, a method is provided for treating sleep apnea, including delivering humidified and cooled air to an individual in need thereof, wherein the humidified and cooled air is produced by a method for humidifying air delivered through a CPAP device as described herein.

In another aspect, a method is provided for treating a lung disease or chronic obstructive respiratory disease (COPD), including delivering humidified oxygen to an individual in need thereof, wherein the humidified oxygen is produced by a method for humidifying oxygen delivered through an oxygen tank by a method as described herein.

In another aspect, a method is provided for treating croup, including delivering humidified air to an individual in need thereof, wherein the humidified air is produced by a method for humidifying air in an environment as described herein.

In another aspect, a method is provided for treating asthma or allergies, including delivering humidified and purified air to an individual in need thereof by a method for humidifying and purifying air in an environment as described herein.

In another aspect, a method is provided for cooling a gas stream, including flowing an input gas stream over a cooling core, wherein the cooling core comprises a frozen material, and wherein the gas stream in contact with the cooling core cools, thereby providing an output gas stream that is a lower temperature than the input gas stream. In an embodiment, the cooling core includes frozen sodium polyacrylate. The cooled gas stream, for example, cooled air or oxygen, may be provided to an individual for whom the cooled gas stream may be beneficial, such as an individual in need of treatment for asthma, hot flashes, or croup, or any other condition for which cooled air or oxygen would be therapeutically beneficial.

In another aspect, a system is provided for humidifying a gas stream, including a device that includes: a housing that contains hydrated SAP; a gas inlet through which the gas stream enters the housing; and a gas outlet through which the an output gas stream exits the housing, wherein the device is configured for the gas stream to flow in contact with the hydrated SAP, and wherein the gas output gas stream comprises a higher humidity than the input gas. In some embodiments, the output gas comprises a cooler temperature than the input gas.

In some embodiments, the input gas is pressurized air supplied by a CPAP device. In some embodiments, the input gas is oxygen supplied by an oxygen tank or an oxygen concentrator.

In some embodiments, the gas inlet and the gas outlet include adaptors for connecting tubing for delivery of the input gas stream or exit of the output gas stream, respectively, wherein the adaptors are retained on the gas inlet and the gas outlet by an inner lip seal, and wherein the adaptors comprise a center post that connects into the gas inlet or the gas outlet and through which the gas stream flows and an outer ring wall configured such that the tubing will not bend the center post when the tubing is connected.

In some embodiments, the system further includes a water trap for collecting condensation that forms in tubing through which the input or the output gas flows.

In some embodiments, the system further includes a device that includes a cooling core, wherein the cooling core includes a frozen material, and wherein the gas stream in contact with the cooling core cools, thereby providing an output gas stream from the system that is a lower temperature than the output gas stream from the system in the absence of the device with the cooling core.

In another aspect, adaptors are provided for connecting tubing for delivery of an input gas stream or exit of an output gas stream, wherein the adaptor is configured to be retained on a gas inlet or a gas outlet by an inner lip seal, and wherein the adaptor includes a center post that connects into the gas inlet or the gas outlet and through which the gas stream flows and an outer ring wall configured such that the tubing will not bend the center post when the tubing is connected.

BRIEF DESCRIPTION OF THE DRAWINGS

FIG. 31 shows an embodiment of a housing with one cool core enclosed therein.

FIG. 32 shows an embodiment of a portable device for humidifying a gas stream, for use with a portable oxygen tank or oxygen concentrator.

FIG. 33 shows an embodiment of a threaded bottom end cap

FIG. 34 shows a cutaway view of the interior of an embodiment of a tubing adaptor.

DETAILED DESCRIPTION

Figure 1:
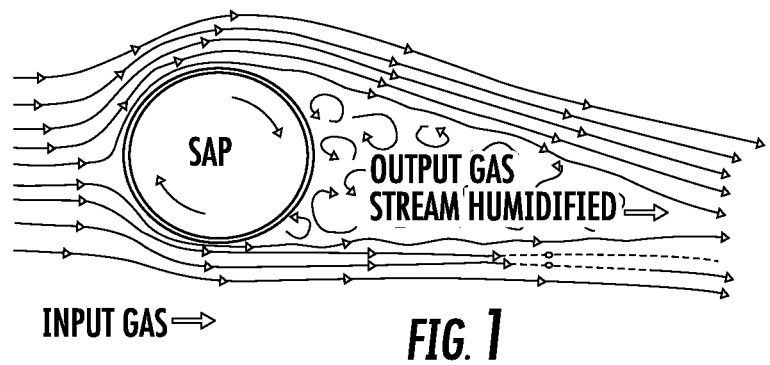
FIG. 1 schematically depicts an embodiment of a gas stream flowing around a spherical SAP particle.

Methods and systems are provided herein in which hydrated superabsorbent polymer materials are used for humidification and cooling of air or another gas stream, such as oxygen. Methods of use are also provided, such as methods of treatment of a condition such as sleep apnea, a respiratory illness, lung disease, COPD, allergies, asthma, or croup, in which delivery of a humidified gas stream, such as humidified air or oxygen, is therapeutically beneficial. The systems described herein can deliver relative humidity, e.g., up to 99%, for improvement in comfort and compliance with pressurized air (e.g., CPAP) and oxygen therapeutic methods.

Definitions

Numeric ranges provided herein are inclusive of the numbers defining the range.

"A," "an" and "the" include plural references unless the context clearly dictates otherwise.

"Superabsorbent polymer" or "SAP" is a polymeric material that has the ability to absorb and retain water or aqueous solutions.

"Relative humidity" is the ratio of the partial pressure of water vapor to the equilibrium vapor pressure of water at a given temperature.

"cmH2O" or "centimeters of water" refers to a unit of air pressure defined as the pressure exerted by a column of water of 1 cm in height at 4° C. (temperature of maximum density) at the standard acceleration of gravity.

"Lpm" or "liters per minute" refers to a volumetric flow rate of a gas. The standard litre per minute (SLM or SLPM) is a unit of volumetric flow rate of a gas corrected to "standardized" conditions of temperature and pressure (STP), temperature of 273.15 K (0° C., 32° F.) and an absolute pressure of exactly $10^5$ Pa (100 kPa, 1 bar).

Superabsorbent Polymers

A superabsorbent polymer (SAP) is polymeric material that absorbs and retains a large amount of water relative to the mass of the polymer, and in the context of the methods and systems described herein, releases water into a flowing gas stream, particularly when the temperature of the gas stream is higher than the temperature of the hydrated SAP.

The SAP hydrates, absorbing up to about 99% water. In some embodiments, a SAP may absorb about 200 to about 600 times its mass in water, e.g., about 30 to about 60 times its volume in water. The swelling capacity of a SAP, or centrifuge retention capacity (CRC), is the amount of 0.9 wt % saline that a SAP can retain under free swelling conditions when surface water has been removed in a centrifuge.

Typically, the polymer backbone in a SAP is hydrophilic, absorbing water due to hydrogen bonding of hydrophilic functional groups to water molecules, which are polar. For example, a SAP may include carboxylic acid functional groups. Carboxylic groups (COO$^-$) may form a salt with positively charged ions, e.g., Na$^+$. The hydrogen atoms of water may be attracted to the COO$^-$ groups, and the oxygen atoms of water may be attracted to the Na$^+$ ions, thus hydrating the SAP.

Energy is released when hydrogen bonds between water molecules are broken and hydrogen bonds are formed between water molecules and the SAP. It takes more energy to separate the water molecules than the amount of energy that is released when the water molecules bond to the SAP. Thus, the temperature is reduced upon hydration of the SAP, in an endothermic process.

In an ionic SAP, e.g., with an ionic group such as carboxylate (COO$^-$) anion, the ionic moieties repel each other. Electrical neutrality is achieved when the ionic group is balanced by an ion of opposite charge, e.g., Nat Upon contact with water, the ions that are not part of the polymer backbone (e.g., Na$^+$) are hydrated, which reduces their attraction to the ionic group of the polymer backbone (e.g., COO$^-$), and allows them to move freely within the polymer network, thus contributing to osmotic pressure within the polymer gel. The mobile ions cannot leave the gel, however, because they are attracted to the ionic groups of the polymer.

In some embodiments, the SAP is crosslinked, forming a hydrogel. The total absorbency and swelling capacity are controlled by the type and degree of crosslinks that are incorporated. Crosslinks between polymer chains form a three-dimensional network and prevent the polymer from swelling indefinitely, which could result in dissolving of the SAP. The crosslinks provide elastic retraction, preventing the polymer chains from swelling to infinite dilution. The degree of crosslinking effects the level of swelling of the polymer and the strength of the polymer network. Increased crosslink density results in decreased swelling capacity and increased polymer gel strength. Nonlimiting examples of crosslinkers include tetraallylethoxy ethane and 1,1,1-trimethylolpropanetriacrylate (TMPTA).

Examples of SAP materials include, but are not limited to, poly-acrylic acid sodium salt (sodium polyacrylate), polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. In some embodiments, the SAP is a 2-propenoic acid (polyacrylate) polymer or copolymer. In one embodiment, the SAP is 2-propenoic acid polymer, crosslinked with sodium 2-propenoate. In some embodiments, the SAP is a polyacrylate salt, such as a sodium, potassium, lithium, or ammonium salt of polyacrylate. In another embodiment, the SAP is a polyacrylate/polyacrylamide salt (e.g., 2-propenoate, potassium salt, polymer with 2-propenamide (acrylamide/potassium acrylate copolymer, crosslinked)).

In general, a SAP for use in the methods described herein is safe for respiratory use and does not support microbial growth. In some embodiments, the SAP includes an antimicrobial substance, for example, but not limited to, an ionic silver solution.

In some embodiments, spherical or substantially spherical SAP particles ("SAP spheres") are used in humidification methods described herein, although other shapes or configurations are not excluded. For example, SAP spheres, e.g., hydrated SAP spheres, may have an average diameter of about 1 mm to about 20 mm.

Although not wishing to be bound by theory, when a SAP such as sodium polyacrylate begins absorbing water molecules, the layers of sodium begin to unfold. The sodium layers pull energy, in the form of heat, from the water to continue expanding, and consequently, the water temperature decreases. When the SAP expands to full hydration, the water stabilizes and maintains the decreased temperature. In an application of use, such as CPAP or oxygen supplementation, pressurized air from the CPAP device or oxygen tank flows over the hydrated SAP. The ambient air or oxygen gas stream is warmer than the water molecules in the SAP. The water in the hydrated SAP absorbs heat from the air or oxygen gas stream and releases water vapor which is picked up and transported in the gas stream, and is then delivered to the nose, throat, and/or mouth of the patient.

Methods for Humidifying a Gas Stream

Methods are provided for humidifying a gas stream, such as air or oxygen. An input gas stream flows over and picks up water vapor from the hydrated SAP, e.g., hydrated 25-100% of the polymer's capacity for water, which is then carried through as a humidified output gas stream. In some embodiments, the hydrated SAP captures heat from the input gas stream, resulting in a humidified output gas stream that is at a higher humidity and a lower temperature than the input gas stream.

The humidified gas stream may be delivered to an individual in need of treatment with a gas, in particular in situations where it is beneficial for the gas stream that is delivered to the individual to be humidified, e.g., for patient comfort, compliance, or therapeutic benefit.

In an embodiment, the SAP is in the form of spherical or substantially spherical particles, and the input gas stream flows around the SAP as shown schematically in FIG. 1.

Figure 2:
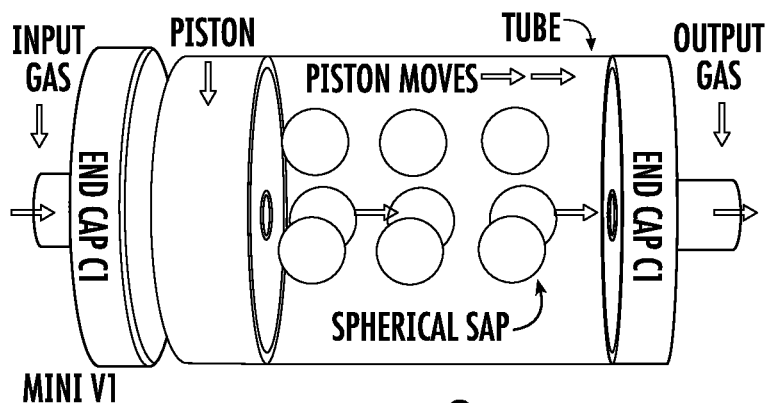
FIG. 2 shows an embodiment of a cylindrical housing with spherical SAP particles enclosed therein.
Figure 13:
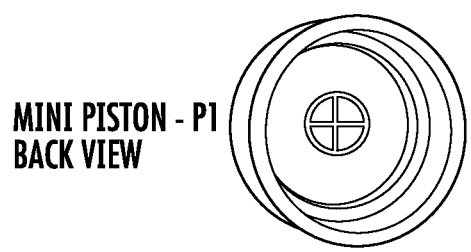
FIG. 13 shows an embodiment of the inner surface of a piston that faces SAP particles in a housing.
Figure 14:
FIG. 14 shows an embodiment of the outer surface of a piston that faces a gas inlet port into which gas is introduced into a housing.
Figure 15:
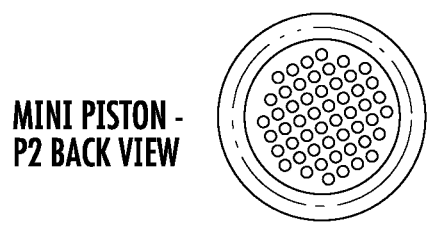
FIG. 15 shows an embodiment of the inner surface of a piston that faces SAP particles in a housing, with a perforated screen therein.
Figure 16:
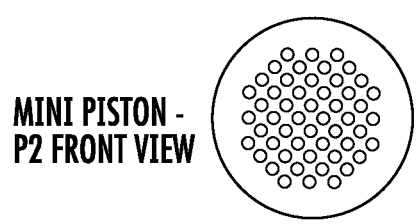
FIG. 16 shows an embodiment of the outer surface of a piston that faces a gas inlet port into which gas is introduced into a housing, with a perforated screen therein.
Figure 17:
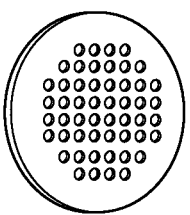
FIG. 17 shows an embodiment of a perforated tube screen.
Figure 18:
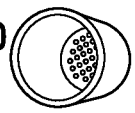
FIG. 18 shows an embodiment of the inner surface of an end cap through which an output gas flows, with a perforated screen therein.
Figure 19:
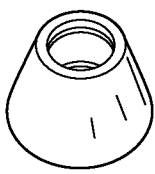
FIG. 19 shows an embodiment of a plug for blocking water flow through a gas inlet or outlet as SAP particles are hydrated.

In some embodiments, the SAP particles, e.g., spherical or substantially spherical particles, are contained within a cylindrical housing and held in place with a "piston" type of design, as shown in FIG. 2. In one embodiment, an input gas may flow through an input gas inlet at a first end of the housing, and output gas may flow through an output gas outlet at a second end of the housing, as shown in FIG. 2. The piston serves to keep the SAP particles compacted, allowing use of the device in different orientations, such as vertical or horizontal. In some embodiments, a mesh or screen is deployed on the piston, to permit air flow but prevent SAP particles from blocking the gas inlet, as shown in FIGS. 13 and 15.

Figure 26:
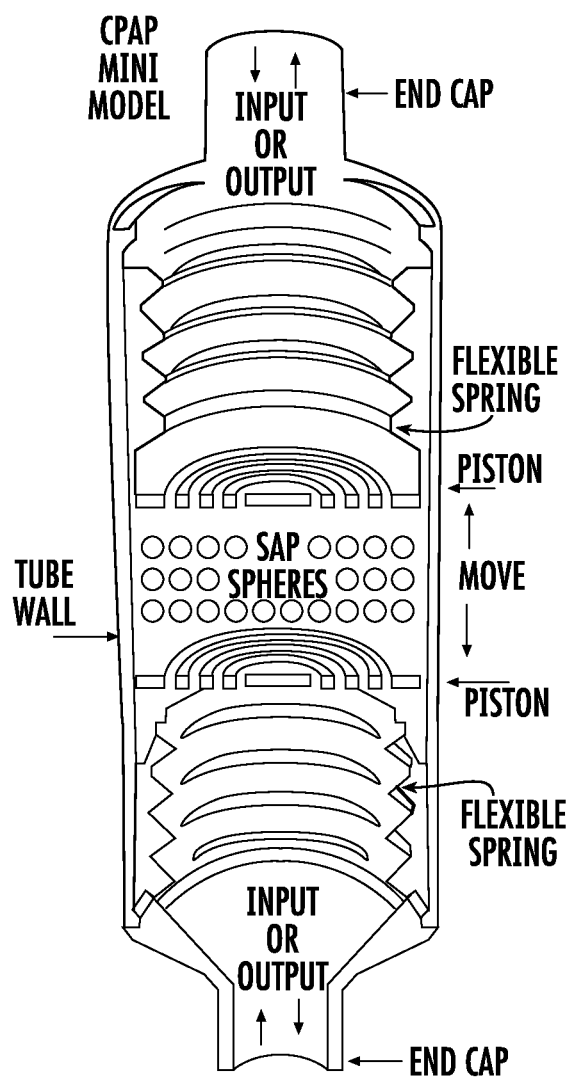
FIG. 26 shows an embodiment of a housing with SAP particles enclosed therein and held in place by two flexible springs.
Figure 27:
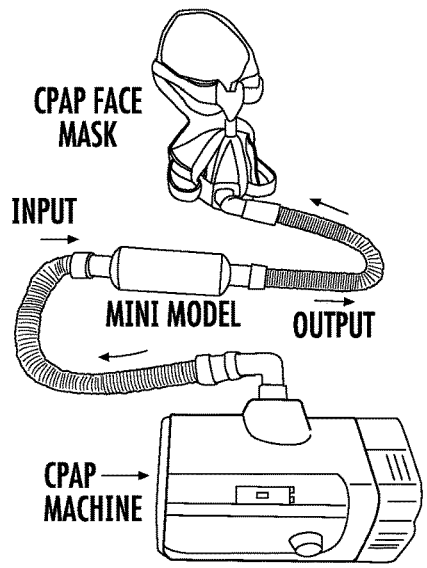
FIG. 27 shows an embodiment of a housing with SAP particles enclosed therein, connected to a CPAP apparatus.
Figure 41:
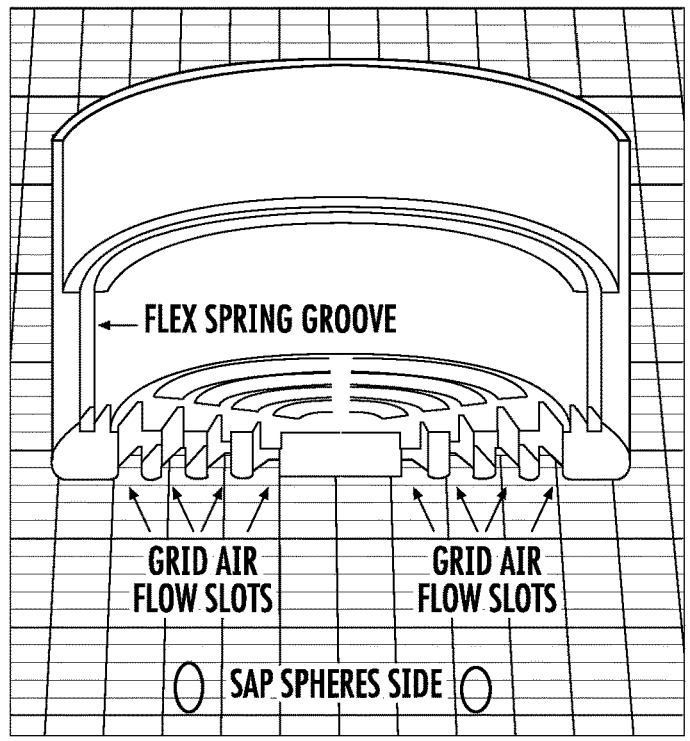
FIG. 41 shows an embodiment of a flexible spring end.

An alternative piston design is depicted in FIG. 26. In this design, SAP particles are held in place between two compressible flexible springs, e.g., two accordion-like, compressible bellows, one at each end of the device, with SAP particles in between, e.g., in the center of the housing. In the design depicted in FIG. 26, both ends of the housing are configured for input or output of a gas stream, such that the device may be used in either orientation between a gas inlet and a gas outlet. Hydrated SAP particles, e.g., spherical or substantially spherical particles, exert compression on the bellows, thereby compressing the flexible spring. An input gas stream flows through the center of the first (input) bellows, picks up water when it contacts the SAP particles, and exits through the second (output) bellows as a hydrated gas stream. The SAP particles decrease in volume as water is removed by the flowing gas stream, thereby allowing the flexible spring to expand, holding the SAP particles in place. In some embodiments, the end of the flexible spring that is adjacent to the SAP particles is constructed of a mesh, grid, or other porous barrier which allows the gas stream to flow, but does not allow SAP particles to exit in the output gas stream. In one embodiment, the end of the flexible spring that is adjacent to the SAP particles is circular with ribs that radiate out from the center and concentric circular ribs that intersect the ribs radiating from the center, as shown schematically in FIG. 41, thereby permitting the gas stream to flow through while providing a barrier to exit of SAP particles in the output gas stream. The flexible springs may be constructed of any flexible material that is suitable for use (e.g., flexible, strong, and durable) in an apparatus as described herein. In some embodiments, flexible springs are constructed of thermoplastic polyurethane (TPU) or thermoplastic elastomer (TPE). In some embodiments, the thickness of the flexible springs is about 0.4 mm to about 0.8 mm, providing a balance between compressibility and air flow. If the springs are too firm, i.e., impeding or delaying decompression, this will significantly decrease or prevent air flow through the device, and may also have the effect of preventing full hydration of SAP particles.

Figure 3:
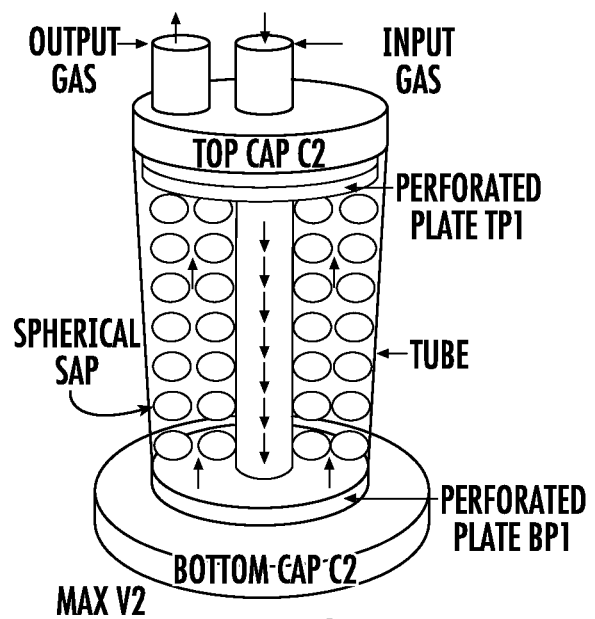
FIG. 3 shows an embodiment of a cylindrical housing with spherical SAP particles enclosed therein.
Figure 20:
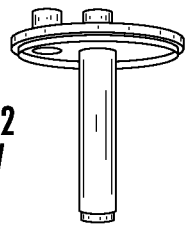
FIG. 20 shows an embodiment of a top end cap into which a housing is inserted, with gas inlet and outlet ports.
Figure 21:
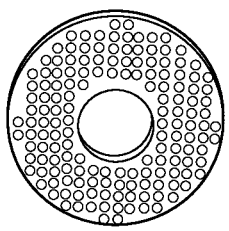
FIG. 21 shows an embodiment of a perforated plate which is situated inside a top end cap.
Figure 28:
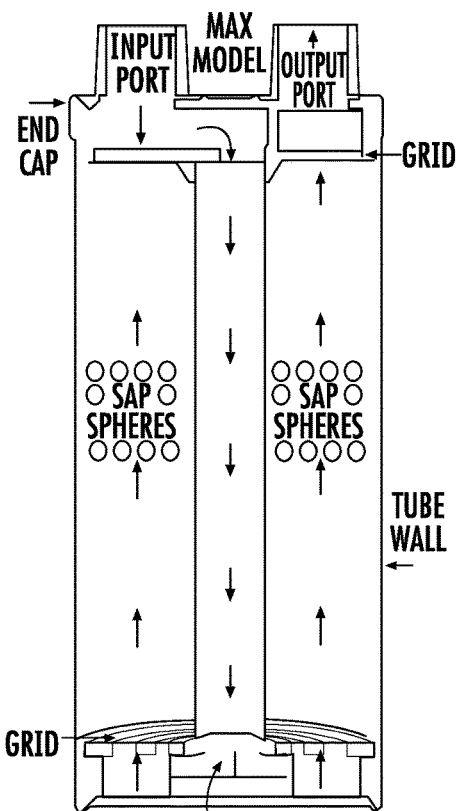
FIG. 28 shows an embodiment of a cylindrical housing with spherical SAP particles enclosed therein.
Figure 29:
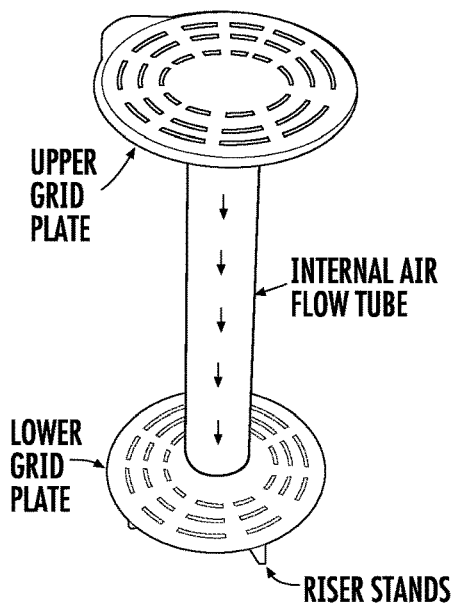
FIG. 29 shows an embodiment of top and bottom grid plates for retention of SAP particles in a housing.

In some embodiments, the SAP particles e.g., spherical or substantially spherical particles, are contained within a cylindrical housing that is maintained in a vertical or substantially vertical orientation, such that the SAP particles are drawn toward the bottom of the device by gravity. An embodiment of such a device is shown in FIG. 3. In one embodiment, a gas inlet and a gas outlet are both at the top of the device, as shown in FIG. 3 and FIG. 20. In some embodiments, perforations or other openings at the top of the device permit air flow but prevent SAP particles from blocking the gas outlet, as shown in FIG. 21. In another embodiment, shown in FIG. 28, a gas inlet and a gas outlet are at the top of the device. Gas flow is through the center of the device, then through hydrated SAP particles to provide a humidified output gas. In some embodiments, grids at the top and bottom of the device retain the SAP particles, as shown in FIG. 29. In some embodiments, a water trap is provided, as shown in FIG. 28, to retain excess condensation, if any, from the SAP particles and prevent the condensation from entering tubing that exits the device, for example, for delivery of the humidified gas stream to an individual.

In some embodiments, shown in FIG. 32, a threaded end cap is provided for recharging SAP particles with water. For example, the threads may be compatible with the threads of a standard size commercially available, e.g., disposable, water bottle, for example, for convenience on the go or when travelling. The bottom of the device may also or alternatively contain a funnel portion for adding water when the SAP particles require rehydration. Further detail of an embodiment of the threaded bottom cap is shown in FIG. 33. In some embodiments, as shown in FIG. 32, the device may contain an opening or slot or "hook hole" for conveniently attaching the device, for example, to a suitcase, or a portable oxygen tank or concentrator.

Figure 4:
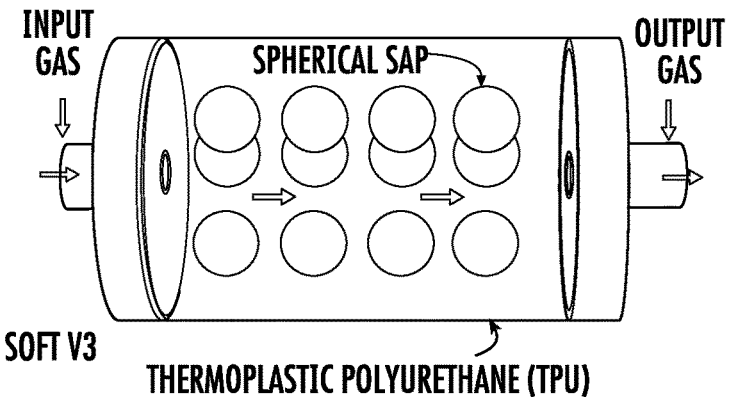
FIG. 4 shows an embodiment of a housing constructed from flexible material, with spherical SAP particles enclosed therein.
Figure 5:
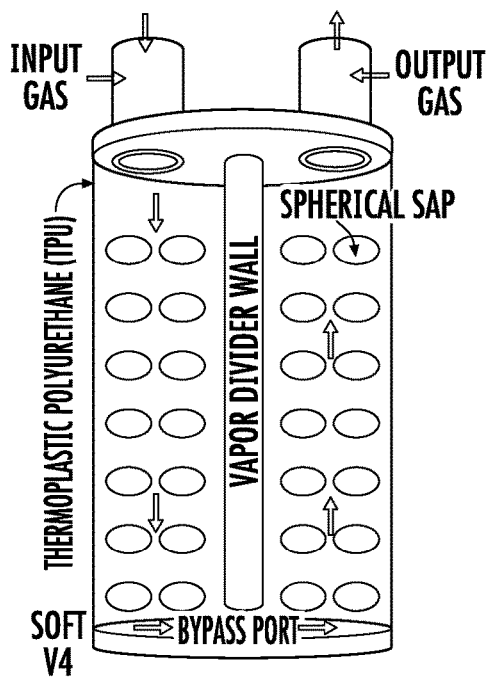
FIG. 5 shows an embodiment of a housing constructed from flexible material, with spherical SAP particles enclosed therein.
Figure 6:
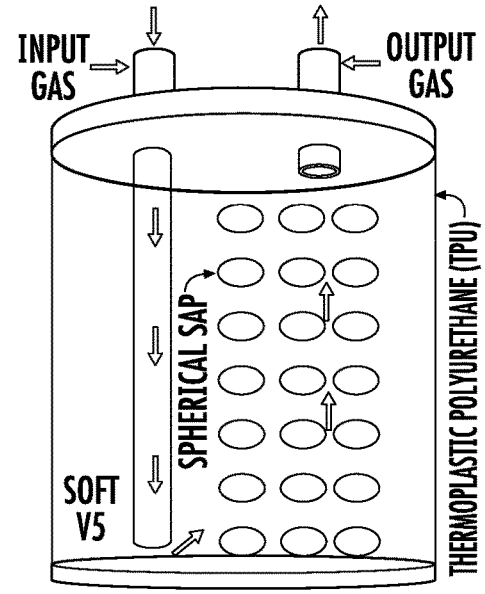
FIG. 6 shows an embodiment of a housing constructed from flexible material, with spherical SAP particles enclosed therein.
Figure 7:
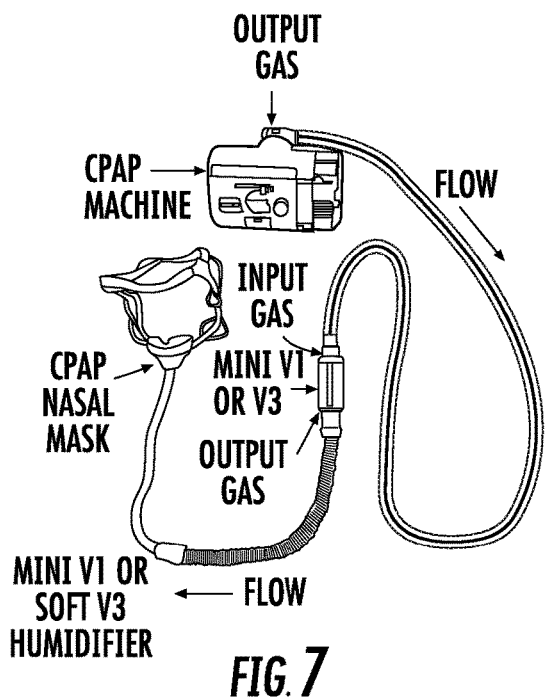
FIG. 7 shows an embodiment of a housing with SAP particles enclosed therein, connected to a CPAP apparatus.
Figure 8:
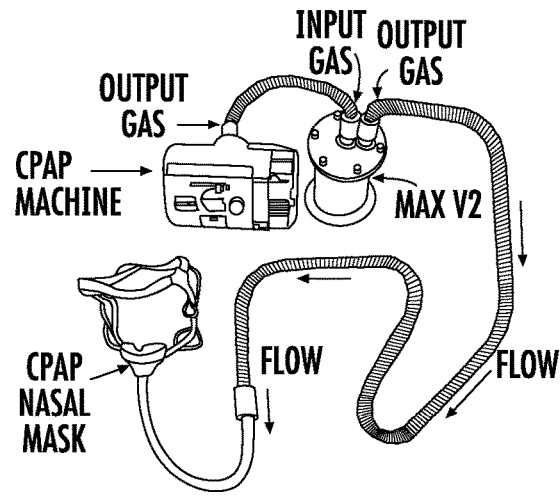
FIG. 8 shows an embodiment of a housing with SAP particles enclosed therein, connected to a CPAP apparatus.
Figure 9:
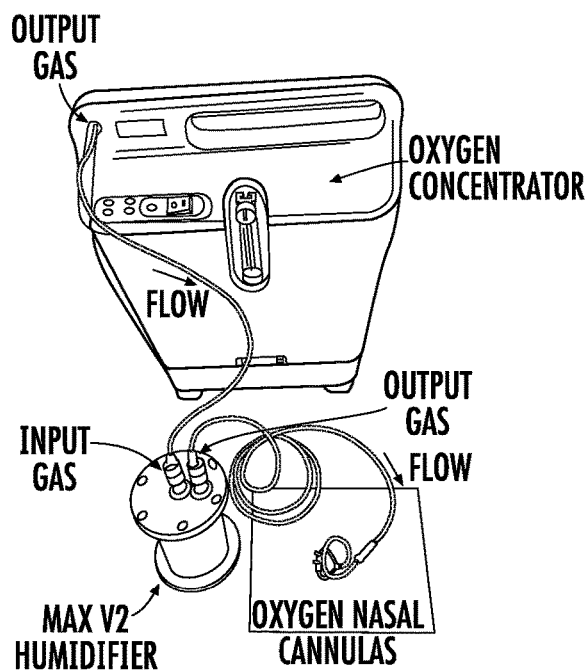
FIG. 9 shows an embodiment of a housing with SAP particles enclosed therein, connected to an oxygen concentrator apparatus.
Figure 10:
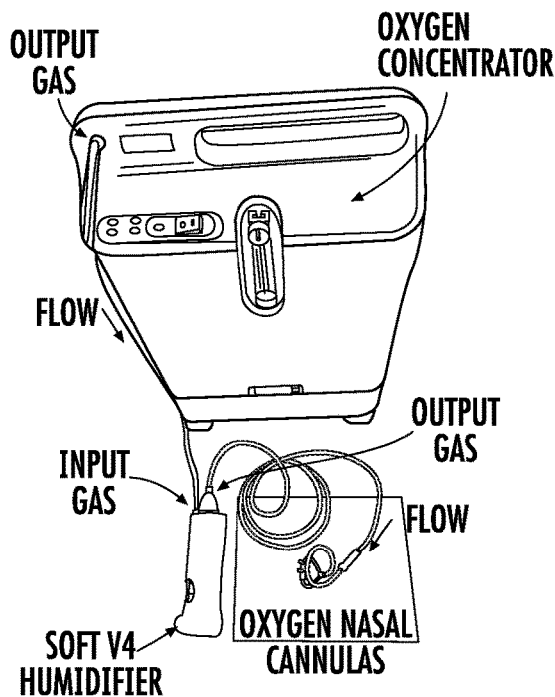
FIG. 10 shows an embodiment of a housing with SAP particles enclosed therein, connected to an oxygen concentrator apparatus.
Figure 11:
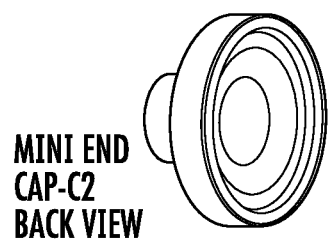
FIG. 11 shows an embodiment of the inside of an end cap into which a housing is inserted.
Figure 12:
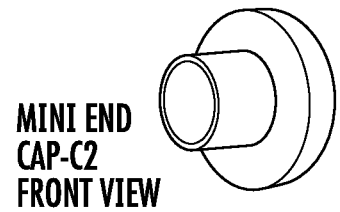
FIG. 12 shows an embodiment of the outside of an end cap into which a housing is inserted.

In some embodiments, a housing for SAP particles, as described herein, is constructed from a rigid material, such as a hard plastic. In other embodiments, the housing is constructed from a flexible material, such as a flexible polymer, e.g., thermoplastic polyurethane (TPU) or thermoplastic elastomer (TPE). Some embodiments in which a flexible housing may be deployed are shown in FIG. 4, FIG. 5, and FIG. 6.

In some embodiments, the input gas stream is at ambient temperature, e.g., about 15° C. to about 30° C. In some embodiments, the relative humidity of the output gas stream is about 85% to about 99%.

The input gas stream can flow over the SAP at any pressure or rate that is suitable for the application of use, such as delivery of a humidified gas stream to an individual. For example, for delivery of air from a CPAP device, the input air stream may flow over the hydrated SAP at about 1 cmH2O to about 30 cmH2O. In another example, for delivery of oxygen, such as from an oxygen tank or an oxygen concentrator, the input oxygen stream may flow over the hydrated SAP at about ½ Lpm to about 15 Lpm.

The output, hydrated gas stream, e.g., hydrated air or oxygen, may flow through tubing for delivery to an individual, for example, into a mask or other device for delivery to the nasal passages, throat, and/or mouth of an individual.

Methods for Cooling a Gas Stream

Methods are provided for cooling a gas stream, such as air or oxygen. A housing is provided that includes one or more cool core(s), a gas inlet, and a gas outlet. The cool core may be composed of, for example, a SAP gel, such as is found in commercially available SAP freezer gel packs, e.g., sodium polyacrylate, or water. The cool core is cooled or frozen prior to use, either inside of or separately from the housing. An input gas stream flows in proximity to or around the cool core, thereby cooling the gas stream, and the output gas is cooler that the input gas. In some embodiments, the output gas is at least about 5° F. or at least about 10° F. cooler than the input gas stream.

Figure 30:
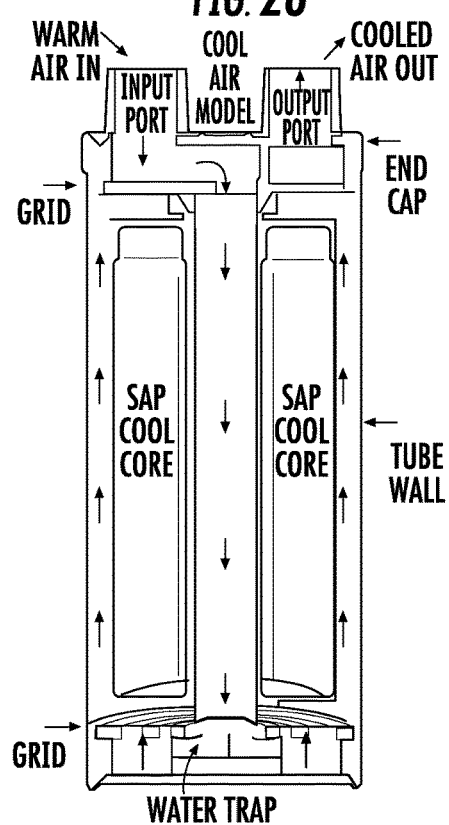
FIG. 30 shows an embodiment of a housing with two cool cores enclosed therein.

In one embodiment, shown in FIG. 30, two cool cores may be provided within a housing, such as a cylindrical or substantially cylindrical housing. The housing includes a gas inlet and a gas outlet. In the embodiment depicted in FIG. 30, both the gas inlet and the gas outlet are at the top of the housing. However, other configurations are contemplated, such as device configurations with gas inlets and outlets as disclosed herein. The input gas (e.g., air, oxygen) flows between the two cool cores, then around the cores along the perimeter of the housing, and then exits at the gas outlet. The output gas is cooler, e.g., at least about 5° F. or at least about 10° F. cooler than the input gas stream. In some embodiments, as depicted in FIG. 30, a water trap is provided to retain excess condensation, if any, from the SAP particles and prevent the condensation from entering tubing that exits the device, for example, for delivery of the humidified gas stream to an individual.

In another embodiment, shown in FIG. 31, one cool core may be provided in a housing, with a gas inlet and a gas outlet at opposite ends of the housing. The input gas (e.g., air, oxygen) flows around the cool core along the perimeter of the housing, and then exits at the gas outlet. The output gas is cooler, e.g., at least about 5° F. or at least about 10° F. cooler than the input gas stream.

In some embodiments, methods are provided for cooling and humidifying a gas stream, such as air or oxygen. A housing including one or more cool core(s) may be used in conjunction with a housing including SAP particles, as described above, to provide humidity and additional cooling capacity. In some embodiments, adding one device with one or more cool core(s) as described herein may cool the gas stream at least about 5° F. or at least about 10° F. more than a device with SAP particles alone. More devices containing cool core(s) may be used if additional cooling of the gas stream is desired. Multiple devices may provide an additive cooling effect. The devices (one or more device(s) with SAP particles and one or more device(s) with cool core(s)) may be joined in series to provide the desired amount of humidity and cooling. In one embodiment, a first device with SAP particles is fluidly connected to and upstream from a second device with cool core(s), and a humidified output gas stream from the first device travels through the second device for further cooling before delivery to an individual.

Methods for Humidifying and Purifying Air

Methods are provided for humidifying, and optionally purifying, air. For example, an input air stream from an environment, such as a room, a building, or an enclosed space, flows over and picks up water from a hydrated SAP, e.g., in a device as disclosed herein, or in a device of alternate design containing hydrated SAP, and through which input air flows in contact with the SAP before exiting the device, producing a humidified output gas stream. In some embodiments, the output humidified air is returned to the environment. In other embodiments, the output humidified air is delivered to an individual in need of humidified air, for example, through tubing, optionally via a mask or other device for delivery to the nasal passages, throat, and/or mouth of the individual.

In some embodiments, particulate matter or other contaminants are removed from the air in conjunction with humidification. For example, a filter may be deployed upstream or downstream from the hydrated SAP. In one embodiment, the filter is a HEPA filter. In some embodiments, pollen may be removed from the air, and a humidified air stream with less pollen than the input air, or with substantially all pollen removed, may be produced.

Tubing Adaptors

Figure 35:
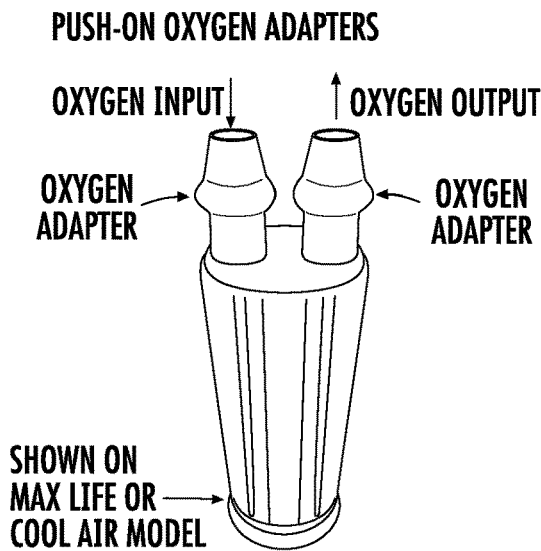
FIG. 35 shows tubing adaptors connected to the gas inlet and outlet of a housing for humidification and/or cooling of a gas stream.

Adaptors are provided for connecting tubing for delivery of a gas stream (e.g., air, oxygen) to or from a device as described herein (e.g., a device with SAP particles or a device with cool core(s)). An embodiment of an adaptor is shown in FIGS. 34 and 35. In contrast to an adaptor that must be inserted into a gas inlet or outlet, the adaptors disclosed herein may be easily pushed onto and pulled off of the inlet and outlet and the tubing easily inserted therein and retained by an inner lip seal. A cutaway interior view of the adaptor is shown in FIG. 34, and adaptors connected to the gas inlet and outlet of a device as disclosed herein are shown in FIG. 35. As shown in FIG. 34, the adaptor includes a center post that connects into the inlet or outlet and through which the gas stream flows, an outer ring wall configured such that the tubing will not bend the center post when the tubing is connected, and a small internal water trap and inner lip seal. In some embodiments, adaptors may be constructed of thermoplastic polyurethane (TPU), thermoplastic elastomer (TPE), or polypropylene (PP).

Water Traps

Figure 36:
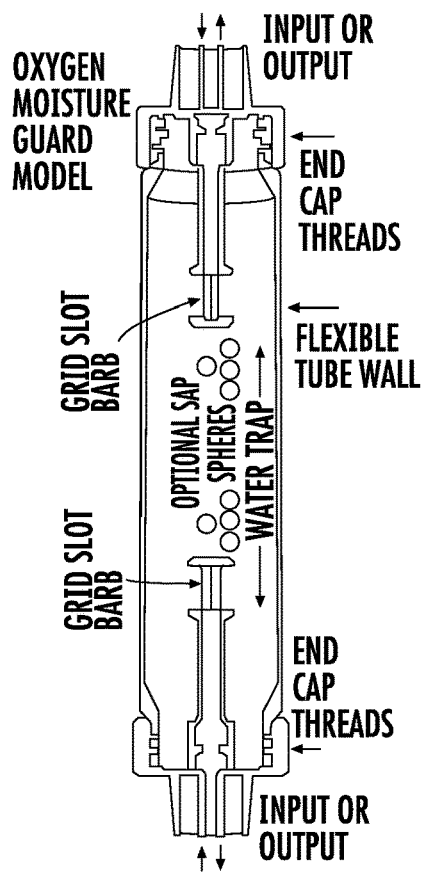
FIG. 36 shows an embodiment of a water trap.
Figure 37:
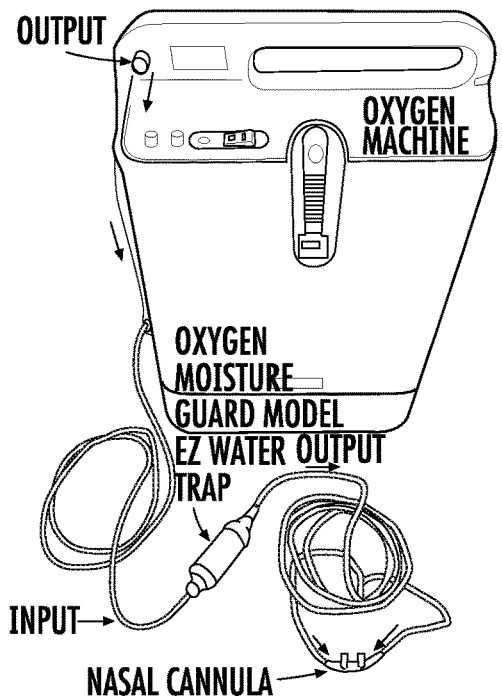
FIG. 37 shows an embodiment of a water trap in line with an oxygen concentrator.
Figure 38:
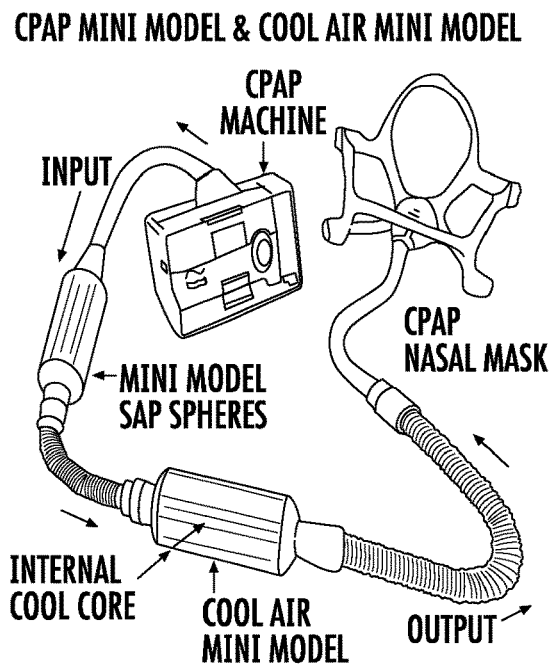
FIG. 38 shows an embodiment of a system that includes a gas stream humidification device upstream from a gas stream cooling device.
Figure 39:
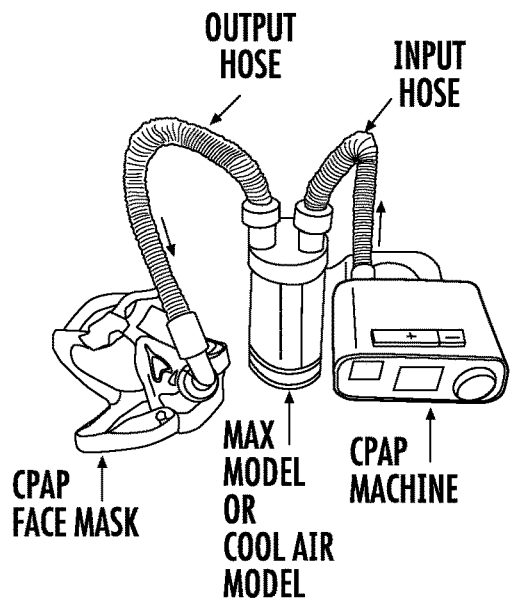
FIG. 39 shows an embodiment of a device with SAP particles or cool cores enclosed therein, connected to a CPAP apparatus.
Figure 40:
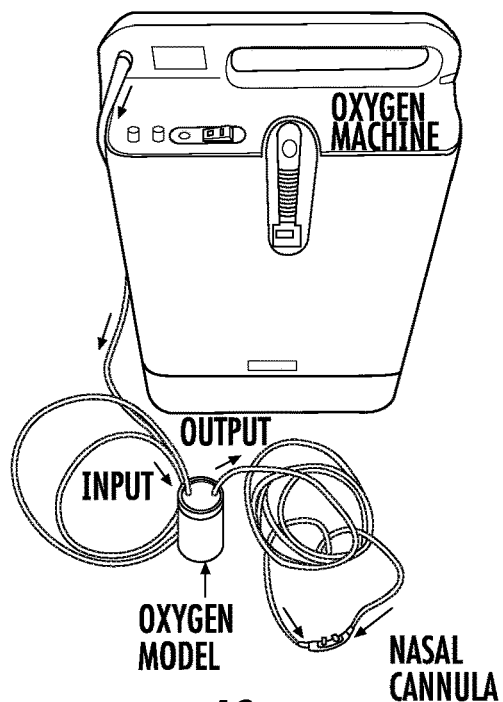
FIG. 40 shows an embodiment of a device with SAP particles or cool cores enclosed therein, connected to an oxygen concentrator.

Water traps are provided for collecting condensation that forms in tubing through which a gas stream flows, such as tubing for a CPAP device or an oxygen tank or concentrator. For example, in certain environments such as cold climates, water may condense inside the tubing and it is advantageous to collet this condensation to prevent its transport with the gas stream that will enter the nasal passages of an individual. An example of a water trap is shown in FIG. 36. In some embodiments, the water trap housing may be constructed of a flexible material, such as thermoplastic polyurethane (TPU) or thermoplastic elastomer (TPE), which is advantageous versus a rigid material such as acrylic that could roll on the floor and become a hazard if an individual steps on it. In some embodiments, the end caps may be constructed from TPU or polypropylene (PP). In some embodiments, the water trap includes a diffuser on each end that contains thin slots (e.g., about 0.25 in. in width) that deflect water and prevent it from entering the tubing that transports a gas stream such as air or oxygen to an individual. In some embodiments, the water trap may contain SAP particles to absorb water in the gas stream as it transits through the water trap. FIG. 37 shows an embodiment of a water trap as described herein in line with an oxygen concentrator.

Methods of Treatment

Conditions for which a humidified gas are therapeutically beneficial may be treated by production and delivery of a humidified gas stream according to any of the methods described herein.

Methods are provided for treatment of sleep apnea. Humidified and cooled air are produced by flowing an input pressurized air stream from a CPAP device over hydrated SAP, as described above. The humidified and cooled air stream are delivered to an individual in need thereof, e.g., an individual suffering from sleep apnea. In some embodiments, the humidified and cooled air are delivered to the individual through tubing that is not heated by an external heating source. In some embodiments, the humidified and cooled output air is delivered at about 1 cmH2O to about 30 cmH2O.

Methods are provided for oxygen therapy. Humidified oxygen is produced by flowing an input oxygen stream, e.g., from an oxygen tank or oxygen concentrator device, over hydrated SAP, as described above. The humidified oxygen stream is delivered to an individual in need thereof, e.g., an individual suffering from COPD or lung disease. In some embodiments, the humidified output oxygen is delivered at about 0.5 Lpm to about 15 Lpm.

Methods are provided for delivery of humidified air to an individual in need thereof. Humidified air is produced by flowing air from an environment over hydrated SAP, as described above. In one embodiment, a method is provided for treating croup, by delivering humidified and cooled air, produced as described herein, to an individual suffering from croup.

Methods are provided for delivery of humidified and purified air to an individual in need thereof. Humidified and purified air is producing by flowing air from an environment of hydrated SAP, as described above, wherein the air is filtered prior to or subsequent to contact with the hydrated SAP. The output air is humidified and contains a lower amount of particulate matter and/or one or more contaminant(s) in comparison to air that has not been filtered. In one embodiment, a method is provided for treating allergies or asthma, by delivering humidified and purified air, produced as described herein, to an individual suffering from asthma or allergies. In some embodiments, filtration of the air reduces or eliminates pollen from the air stream.

Methods are provided for delivery of cooled air or oxygen to an individual in need thereof. Cooled air or oxygen is produced by flowing the gas stream in proximity to or around one or more cool core(s), as described herein. The output gas stream is cooler than an equivalent gas stream that has not been routed through a device with cool core(s). In some embodiments, a method is provided for treating asthma, hot flashes, croup, or any other condition for which breathing cool air or oxygen would be beneficial. In some embodiments, the cooled air or oxygen stream is humidified, for example, with an upstream unit for humidification of the gas stream as described herein.

Systems

Systems are provided for use in methods for humidifying a gas stream as described herein and in methods of treatment of conditions for which a humidified gas, such as air or oxygen, would be beneficial. Systems herein include a housing for retaining hydrated SAP, through which in input gas stream may flow, configured such that the input gas contacts the hydrated SAP and picks up water molecules in the form of water vapor as it flows through the housing. The housing includes an inlet through which an input gas stream enters the housing, and includes an outlet through which the hydrated output gas stream exits the housing.

In some embodiments, the housing includes spherical or substantially spherical hydrated SAP particles contained therein. In some embodiments, the housing is cylindrical or substantially cylindrical, or may have a cylindrical or substantially cylindrical portion in which the hydrated SAP is contained. The housing may be constructed of a rigid material or a flexible material.

The input gas stream may enter the housing through input tubing, and the humidified output gas stream may exit the housing through output tubing. In some embodiments, the input gas stream may be supplied by a device to provide pressurized air, such as a CPAP device, or may be supplied by a device to provide oxygen, such as an oxygen tank or an oxygen concentrator. In some embodiments, output tubing is connected to a mask or other device for delivering the humidified output gas stream to the nasal passages, throat, and/or mouth of an individual.

Figure 22:
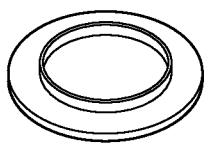
FIG. 22 shows an embodiment of a bottom end cap into which a housing is inserted.
Figure 23:
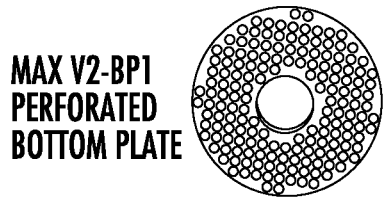
FIG. 23 shows an embodiment of a perforated plate which is situated inside a bottom end cap.

In some embodiments, the input gas stream may be air from an environment, such as a room, a building, an enclosure, or outdoor air. An air humidification device may include a component, such as a blower motor, to draw input air into the device and push the air through the housing that contains hydrated SAP. Optionally, a filter may be included in the air humidification device, either upstream or downstream from the hydrated SAP, to remove impurities from the air, such as pollen and/or other particulate matter, thereby providing a humidified and purified output air stream. In one embodiment, the filter is a HEPA filter. Optionally, the output gas stream may flow through an outlet and into tubing that is connected to a mask or other device for delivering the humidified and optionally purified air to the nasal passages, throat, and/or mouth of an individual. In one embodiment, the input air flows through, in sequence, one or more filter (e.g., including a HEPA filter), a blower motor, a housing containing hydrated SAP, and optionally, tubing connected to a mask or other device for delivery of the output air to an individual.

In one embodiment, depicted schematically in FIG. 2, an input gas enters the housing at a first end that contains a gas inlet, and an output gas exits the housing at a second end that contains a gas outlet. The output gas is higher humidity, and in some embodiments, a cooler temperature, than the input gas. In the embodiment shown in FIG. 2, the gas inlet and the gas outlet are at opposite ends of the cylindrical housing. An embodiment of end caps that contain a gas inlet or outlet port are shown in FIG. 11 and FIG. 12. The housing may include an internal piston, proximal to the gas inlet and movable toward the gas outlet in response to gas pressure, for retention of the SAP particles. The gas stream travels from inlet to outlet, over and around the SAP particles, and the piston responds to pressure from the flowing input gas stream, compacting and holding the SAP particles in place. The gas pressure moves the piston, keeping the SAP particles compressed, permitting use of the device in any orientation, including horizontal or vertical or at angles in between. As water from the hydrated SAP enters the flowing gas stream, the SAP particles shrink and the piston moves accordingly toward the gas outlet, compressing the SAP. One embodiment of a piston is shown in FIG. 13 and FIG. 14. An opening is provided to which a mesh screen may be affixed, thereby permitting gas flow while blocking SAP particles from entering the gas inlet. Another embodiment of a piston is shown in FIG. 15 and FIG. 16. A perforated surface, i.e., containing a plurality of openings, is provided, thereby permitting gas flow while blocking SAP particles from entering the gas inlet. In some embodiments, a screen or other perforated surface, as shown in FIG. 17, is provided at the second end, e.g., within the end cap at the second end, to block egress of SAP particles into the gas outlet. In some embodiments, a screen or other perforated surface is provided at the gas outlet, e.g., as shown in FIG. 18, to block egress of SAP particles through the gas outlet. The housing, piston, and/or end caps may be constructed of any suitable material, such as a rigid plastic. In one embodiment, the housing may be transparent, or alternatively may be opaque, or alternatively may be opaque with a transparent window or strip through which the SAP particles may be viewed.

In another embodiment, depicted schematically in FIG. 3, a housing contains a first, top end and a second, bottom end, wherein the device is configured in vertical or substantially vertical configuration during operation, and the top end is above the bottom end. The top end contains a gas inlet and a gas outlet. An input gas enters the housing at the gas inlet and an output gas exits the housing at the gas outlet. The output gas is higher humidity, and in some embodiments, a cooler temperature, than the input gas. The input gas stream travels through a tube or other passage in a direction from the top to the bottom of the device. An example of a top cap with an inlet tube is shown in FIG. 20. In some embodiments, the device is held in a vertical configuration with a bottom cap into which the housing is inserted, for example, as shown in FIG. 22. In some embodiments, the input gas stream flows through a perforated surface at or near the bottom of the housing and flows back up through the perforations to contact SAP particles contained within the housing. An example of a perforated bottom plate is shown in FIG. 23. The gas stream flows up through the SAP, and exits through the gas outlet as a humidified gas stream. In some embodiments, a top cap with an interior perforated plate is used, as shown in FIG. 21, which prevents SAP particles from exiting the device through the gas outlet. In one embodiment, the housing may be transparent, or alternatively may be opaque, or alternatively may be opaque with a transparent window or strip through which the SAP particles may be viewed.

Figure 24:
FIG. 24 shows an embodiment of the inside of an end cap into which a housing is inserted.
Figure 25:
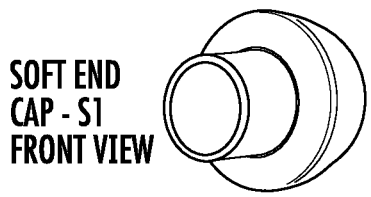
FIG. 25 shows an embodiment of the outside of an end cap into which a housing is inserted.

In another embodiment, depicted schematically in FIG. 4, an input gas enters the housing at a first end that contains a gas inlet, and an output gas exits the housing at a second end that contains a gas outlet. In the embodiment shown in FIG. 4, the gas inlet and the gas outlet are at opposite ends of the cylindrical housing. The gas stream travels from inlet to outlet, over and around the SAP particles. An embodiment of end caps that contain a gas inlet or outlet port are shown in FIG. 24 and FIG. 25. In some embodiments the end caps include an internal built in mesh or screen. The housing is constructed of a flexible material. For example, the flexible material may be TPU or any other suitable flexible, soft material that is strong and durable for use in the methods described herein. In some embodiments, a device as depicted in FIG. 4 may be constructed for short term or disposable use. In some embodiments, device does not include a piston. In some embodiments, the SAP particles in a flexible housing do not dissipate heat as fast as in a rigid housing, and therefore they don't shrink as fast, reducing or eliminating the need for a piston or other device to compress and/or hold them in place.

In another embodiment, depicted schematically in FIG. 5, a housing contains a first, top end and a second, bottom end, wherein the device is configured in vertical or substantially vertical configuration during operation, and the top end is above the bottom end. The top end contains a gas inlet and a gas outlet. An input gas enters the housing at the gas inlet and an output gas exits the housing at the gas outlet. The output gas is higher humidity, and in some embodiments, a cooler temperature, than the input gas. The housing includes a divider wall or separator that is connected to a top plate that contains the gas inlet and the gas output, configured on different sides of the separator. The separator extends from the top plate downward toward a bottom plate, creating two chambers, one on each side of the separator, i.e., a first chamber beneath the gas inlet and a second chamber beneath the gas outlet, and leaving an opening at the bottom of the housing to create a bypass port. SAP particles are contained on both sides of the separator. In some embodiments, the opening of the bypass port is too small for SAP particles to travel between the two chambers on either side of the separator, e.g., smaller than the diameter of the SAP particles. The input gas stream flows through the gas inlet and through the first chamber in a direction from top to bottom of the housing, through the bypass port, and then through the second chamber in a direction from bottom to top of the housing, exiting as a humidified output gas through the gas outlet. The housing may be constructed of a flexible material, for example, TPU or another suitable flexible material. In some embodiments, a device as depicted in FIG. 5 may be constructed for short term or disposable use. In some embodiments, a perforated screen or mesh is deployed between the separator and the bottom of the device, to prevent SAP particles from entering and blocking the bypass port.

In another embodiment, depicted schematically in FIG. 6, a housing contains a first, top end and a second, bottom end, wherein the device is configured in vertical or substantially vertical configuration during operation, and the top end is above the bottom end. The top end contains a gas inlet and a gas outlet. An input gas enters the housing at the gas inlet and an output gas exits the housing at the gas outlet. The output gas is higher humidity, and in some embodiments, a cooler temperature, than the input gas. The input gas stream travels through a tube or other passage in a direction from the top to the bottom of the device. The input gas tube or passage extends from the top plate downward toward a bottom plate, leaving an opening at the bottom of the housing. SAP particles surround the input gas tube or passage. The input gas stream flows through the gas inlet in a direction from top to bottom of the housing, exits the bottom of the input gas tube or passage, and then through the SAP particles in a direction from bottom to top of the housing, exiting as a humidified output gas through the gas outlet. The housing may be constructed of a flexible material, for example, TPU or another suitable flexible material. In some embodiments, a device as depicted in FIG. 6 may be constructed for short term or disposable use.

In another embodiment, depicted schematically in FIG. 26, an input gas enters the housing at a first end or a second end, wherein both ends are configured for either a gas inlet or a gas outlet, and exits the end opposite the gas input. The output gas is higher humidity, and in some embodiments, a cooler temperature, than the input gas. The housing may include two flexible springs, which serve as internal pistons, one proximal to the gas inlet and one proximal to the gas output. The springs respond to gas pressure, for retention of the SAP particles. The gas stream travels from inlet to outlet, over and around the SAP particles, the piston proximal to the gas inlet expands in response to pressure from the flowing input gas stream, and the piston proximal to the gas outlet compresses, compacting and holding the SAP particles in place. The gas pressure moves the pistons, keeping the SAP particles compressed, permitting use of the device in any orientation, including horizontal or vertical or at angles in between. As water from the hydrated SAP enters the flowing gas stream, the SAP particles shrink and the pistons move accordingly toward the gas outlet, compressing the SAP. Openings at distal ends of each piston (the end of the piston that is adjacent to SAP particles) are provided, which may contain a mesh or other perforated or porous openings, thereby permitting gas flow while blocking SAP particles from entering the gas inlet. In one embodiment, the end of the flexible spring that is adjacent to the SAP particles is circular with ribs that radiate out from the center and concentric circular ribs that intersect the ribs radiating from the center, thereby permitting the gas stream to flow through while providing a barrier to exit of SAP particles in the output gas stream.

In another embodiment, depicted schematically in FIG. 28, a housing contains a first, top end and a second, bottom end, wherein the device is configured in vertical or substantially vertical configuration during operation, and the top end is above the bottom end. The top end contains a gas inlet and a gas outlet. An input gas enters the housing at the gas inlet and an output gas exits the housing at the gas outlet. The output gas is higher humidity, and in some embodiments, a cooler temperature, than the input gas. The input gas stream travels through a tube or other passage in a direction from the top to the bottom of the device. The input gas tube or passage extends from the top plate downward toward a bottom plate, leaving an opening at the bottom of the housing. SAP particles surround the input gas tube or passage. The input gas stream flows through the gas inlet and is routed through a center tube, in a direction from top to bottom of the housing, exits the bottom of the input gas tube or passage, and then traverses through the SAP particles in a direction from bottom to top of the housing, exiting as a humidified output gas through the gas outlet. In some embodiments, the device includes top and bottom grid plates, as depicted in FIG. 29.

In another embodiment, depicted schematically in FIG. 32, a housing contains a first, top end and a second, bottom end, wherein the device is configured in vertical or substantially vertical configuration during operation, and the top end is above the bottom end. The top end contains a gas inlet and a gas outlet. An input gas enters the housing at the gas inlet and an output gas exits the housing at the gas outlet. The output gas is higher humidity, and in some embodiments, a cooler temperature, than the input gas. The input gas stream travels through a tube or other passage in a direction from the top to the bottom of the device. The input gas tube or passage extends from the inlet downward toward the bottom of the device, contacting SAP particles. The device contains diffusers, e.g., with slots for passage of the gas stream at the bottom of the device and proximal to the outlet, as shown in FIG. 32, thereby reducing or preventing water from entering the gas line through which the gas will be delivered to an individual. The gas stream exits as a humidified output gas through the gas outlet.

An embodiment in which a device as shown in FIG. 2 or FIG. 4 used in conjunction with a CPAP device is shown in FIG. 7. An embodiment in which a device as shown in FIG. 3 is used in conjunction with a CPAP device is shown in FIG. 8. An embodiment in which a device as shown in FIG. 26 is used in conjunction with a CPAP device is shown in FIG. 27. An embodiment in which a device as shown in FIG. 28 is used in conjunction with a CPAP device is shown in FIG. 39. A pressurized air stream flows through tubing to the SAP containing housing as described herein, flows from the inlet to the outlet through the housing as described herein, whereby the air stream picks up water from the hydrated SAP and becomes a humidified air stream, which flows through the outlet of the housing and then through tubing to a nasal mask, through which the humidified, pressurized air is delivered to an individual, for example, for CPAP therapy for a condition such as sleep apnea.

An embodiment in which a device as shown in FIG. 3 is used in conjunction with an oxygen concentrator is shown in FIG. 9. An embodiment in which a device as shown in FIG. 5 or FIG. 6 is used in conjunction with an oxygen concentrator is shown in FIG. 10. An embodiment in which a device as shown in FIG. 32 is used in conjunction with an oxygen concentrator is shown in FIG. 40. An pressurized oxygen steam flows through tubing to the SAP containing housing as described herein, flows from the inlet to the outlet through the housing as described herein, whereby the oxygen stream picks up water from the hydrated SAP and becomes a humidified oxygen stream, which flows through the outlet of the housing and then through tubing to nasal cannulas, through which the humidified, pressurized oxygen is delivered to an individual, for example, for respiratory therapy.

Systems are provided for use in methods for cooling a gas stream as described herein and in methods of treatment of conditions for which a cooled gas, such as air or oxygen, would be beneficial. A system for cooling a gas stream may include a device with one or more cool core(s), for example, as shown in FIGS. 30 and 31. The device with cool core(s) may be used alone or may be used in conjunction with a device for humidification of the gas stream. For example, a device that includes SAP particles may be included in conjunction with, e.g., upstream from, the device with cool core(s). An example of such a system is shown in FIG. 38.

In some embodiments of the devices herein, the housing, piston, and/or end caps are constructed from a rigid plastic material, such as polycarbonate, acetal, TPU, acrylic plastic, and/or polypropylene. In one embodiment, the housing is constructed from polycarbonate, such as 1/16 inch thickness polycarbonate. In one embodiment, the piston and/or end caps are constructed from acetal. In another embodiment, the piston and/or end caps are constructed from polypropylene. In some embodiments, the end caps contain an internal o-ring washer, for example, constructed of silicone, that is held in place by tubing in an application of use.

In some embodiments of the devices herein, the housing and/or internal separator is constructed from a flexible material, such as TPU or TPE. In one embodiment, the end caps are constructed from acetal. In some embodiments, the end caps include internal mesh screens constructed from polypropylene. In some embodiments, gas input and output fittings are constructed form polypropylene.

SAP may be hydrated in any of the devices described herein by adding water, e.g., distilled or filtered water, although tap water may also be used, to submerge the SAP for a period of time (e.g., 6-8 hours), and then decanting the excess water that has not been absorbed by the polymer. After using the device to humidify a gas stream, the SAP particles will shrink as water is removed into the flowing gas stream, and the SAP must be rehydrated by again submerging in water (e.g., 3-5 hours) and decanting the excess.

In embodiments of devices that may be used in a horizontal orientation, such as the device shown in FIG. 2, a service cap may be provided, such as shown in FIG. 19, to plug off a gas port when rehydrating SAP contained in the housing. This allows the device to be held in a vertical orientation while adding water to hydrate the SAP. The service cap may include a seal to block the water from flowing out of the device during rehydration.

In some embodiments, a device may include a water trap, e.g., as shown in FIG. 28, to collect excess condensation from SAP particles, if any, for example, during operation of the device.

In some embodiments, a device may include a threaded end cap and/or funnel to facilitate recharging of SAP particles therein. For example, the threads may be configured such that a commercially available disposable water bottle may be engaged to pour water into the interior of the device, providing convenience when travelling. An embodiment of a threaded end cap is shown in FIG. 33.

In some embodiments, a device may include an opening, as shown in FIG. 32, ("Hook Hole"), for example, for ease of attachment to a mobile apparatus such as an oxygen tank or oxygen concentrator.

In some embodiments, a system as described herein may include an inline water trap, for example, as shown in FIG. 36, to collect condensation. An embodiment of a water trap in a system that includes an oxygen concentrator is shown in FIG. 37. The inline water trap may be constructed of a flexible material, and may optionally include SAP particles.

The following examples are intended to illustrate, but not limit, the invention.

EXAMPLES

Example 1

Humidification and Cooling of Pressurized Air Delivered Through CPAP Device

Ambient room humidity and temperature were determined using a wireless sensor in a test chamber ("Ambient"). Humidity and temperature were then determined for output air delivered from a CPAP machine with six feet of non-heated tubing ("CPAP"). Finally, humidity and temperature were determined for air delivered from a CPAP machine with pressurized air traveling through an inline device that contained hydrated SAP spheres with two feet of tubing between the air source and the inline device, then six feet of tubing downstream from the device and through which the output air was delivered ("Max V2"). The air pressure delivered from the CPAP device was 10 cmH2O. Results are shown in Table 1.

TABLE 1

| Condition | Temperature (° F.) | Relative Humidity |
|---|---|---|
| Ambient | 67.1 | 56.7 |
| CPAP | 74 | 47 |
| Max V2 | 63 | 91.1 |

When heated tubing was used for the CPAP test instead of non-heated tubing, the humidity dropped lower and the temperature rose higher than shown in Table 1 for the "CPAP" test condition (data not shown).

Example 2

Humidification of Oxygen Delivered Through an Oxygen Concentrator Machine

Ambient room humidity and temperature were determined using a wireless sensor in a test chamber ("Ambient"). Humidity and temperature were then determined with oxygen delivered from an oxygen concentrator machine through twenty-five feet of oxygen tubing ("Oxygen Concentrator"). Finally, humidity and temperature were determined for oxygen delivered from an oxygen concentrator machine with oxygen traveling through an inline device that contained hydrated SAP spheres with twenty-five feet of oxygen tubing between the air source and the inline device, then seven feet of oxygen tubing downstream from the device and through which the output oxygen was delivered ("Max V2"). The flow rate of oxygen delivered from the oxygen concentrator device was 4 Lpm. Results are shown in Table 2.

TABLE 2

| Condition | Temperature (° F.) | Relative Humidity |
|---|---|---|
| Ambient | 65.4 | 63.2 |
| Oxygen Concentrator | 65.7 | 1.2 |
| Max V2 | 65.8 | 98.1 |

Example 3

Humidification of Oxygen Delivered Through an Oxygen Concentrator Machine

Ambient room humidity and temperature were determined using a wireless sensor in a test chamber ("Ambient"). Humidity and temperature were then determined with oxygen delivered from an oxygen concentrator machine using an in-line wireless sensor in a test chamber ("Oxygen Concentrator"). Finally, humidity and temperature were determined for oxygen delivered from an oxygen concentrator machine with oxygen traveling through an inline device that contained hydrated SAP spheres as shown in FIG. 32 using an in-line wireless sensor in a test chamber ("Oxygen Humidifier Output"). The flow rate of oxygen delivered from the oxygen concentrator device was 4 Lpm. Results are shown in Table 3.

TABLE 3

| Condition | Temperature (° F.) | Relative Humidity |
|---|---|---|
| Ambient | 65.4 | 63.2 |
| Oxygen Concentrator | 69.7 | 1.2 |
| Oxygen Humidifier Output | 65.4 | 87.1 |

Example 4

Humidification and Cooling of Pressurized Air Delivered Through CPAP Device

Ambient room humidity and temperature were determined using a wireless sensor in a test chamber ("Ambient"). Humidity and temperature were then determined for output air delivered from a CPAP machine using an in-line wireless sensor in a test chamber ("CPAP"). Finally, humidity and temperature were determined for air delivered from a CPAP machine with pressurized air traveling through an inline device that contained hydrated SAP spheres as shown in FIG. 28 using an in-line wireless sensor in a test chamber ("CPAP Humidifier Output"). The air pressure delivered from the CPAP device was 10 cmH2O. Results are shown in Table 4.

TABLE 4

| Condition | Temperature (° F.) | Relative Humidity |
|---|---|---|
| Ambient | 67.1 | 56.7 |
| CPAP | 74 | 47 |
| CPAP Humidifier Output | 63 | 97.7 |

Although the foregoing invention has been described in some detail by way of illustration and examples for purposes of clarity of understanding, it will be apparent to those skilled in the art that certain changes and modifications may be practiced without departing from the spirit and scope of the invention, which is delineated by the appended claims. Therefore, the description should not be construed as limiting the scope of the invention.

All publications, patents, and patent applications cited herein are hereby incorporated by reference in their entireties for all purposes and to the same extent as if each individual publication, patent, or patent application were specifically and individually indicated to be so incorporated by reference.

We claim:

1. A method for humidifying air or oxygen, comprising:
flowing an input gas stream through a bed of hydrated superabsorbent polymer (SAP), wherein the SAP is a crosslinked polyacrylate/polyacrylamide copolymer,
wherein the SAP is in the form of a plurality of substantially spherical units,
wherein the input gas stream flows around and in direct contact with the spherical units such that water from the hydrated SAP enters the input gas stream, thereby providing a humidified output gas stream, and wherein the hydrated SAP captures heat from the input gas stream, and wherein the humidified output gas stream is a lower temperature than the input gas stream.

2. The method according to claim 1, wherein the humidified output gas stream comprises a relative humidity of about 85% to about 99%.

3. The method according to claim 1, wherein the SAP comprises ionic silver.

4. The method according to claim 1, wherein the hydrated SAP is retained in a housing through which the input gas stream flows, and wherein the pressure at which the input gas stream flows over the hydrated SAP is about 1 $cmH_2O$ to about 30 $cmH_2O$.

5. A method according to claim 1, further comprising flowing the output gas stream through a device that comprises a cooling core, wherein the cooling core comprises a frozen material,
wherein the gas stream in contact with the cooling core cools, thereby providing an output gas stream that is a lower temperature than the output gas stream in the absence of the device with the cooling core.

6. The method of claim 1, wherein the SAP is crosslinked with sodium 2-propenoate.

7. A method for humidification of air delivered through a continuous positive airway pressure (CPAP) device, comprising the method of claim 1, wherein the input gas stream is air and wherein the humidified output gas stream is humidified air, and wherein the humidified air is delivered through tubing to an individual in need thereof.

8. The method according to claim 7, wherein the tubing is not heated from an external heating source.

9. The method according to claim 8, wherein the pressure of the output gas stream is about 1 $cmH_2O$ to about 30 $cmH_2O$.

10. A method for treating sleep apnea, comprising delivering humidified and cooled air to an individual in need of sleep apnea treatment by a method according to claim 7.

11. A method for humidification of oxygen delivered from an oxygen tank, comprising the method of claim 1, wherein the input gas stream is oxygen and wherein the humidified output gas stream is humidified oxygen, and wherein the humidified oxygen is delivered through tubing to an individual in need thereof.

12. The method according to claim 11, wherein the flow rate of the output gas stream is about 0.5 Lpm to about 15 Lpm.

13. A method for treating lung disease or chronic obstructive respiratory disease (COPD), comprising delivering humidified and cooled oxygen to an individual in need of lung disease or COPD treatment by a method according to claim 11.

14. A method for humidifying air in an environment, comprising the method of claim 1, wherein the input gas stream is air from the environment and wherein the output gas stream is humidified air.

15. A method for treating croup, comprising delivering humidified air to an individual in need of treatment for croup by a method according claim 14.

16. A method for humidifying and purifying air in an environment, comprising the method of claim 1, wherein the input gas stream is air from the environment that comprises contaminants and/or particulate matter, wherein the air is filtered prior to or after contact with the hydrated SAP, and wherein the humidified output gas stream comprises a reduced number of contaminants and/or particulate matter in comparison with the input air stream.

17. A method for treating asthma or allergies, comprising delivering humidified and purified air to an individual in need of treatment for asthma or allergies by a method according claim 16.

18. A system for humidifying a gas stream, comprising:
a device that comprises a housing that comprises a bed of hydrated SAP, wherein the SAP is a crosslinked polyacrylate/polyacrylamide copolymer, and wherein the SAP is in the form of a plurality of substantially spherical units; a gas inlet through which an input gas stream is configured to enters the housing; and a gas outlet through which an output gas stream is configured to exit the housing, wherein the device is configured for the input gas stream to flow through the bed of hydrated SAP such that the input gas stream flows around and in direct contact with the hydrated SAP spherical units, such that the output gas stream comprises a higher humidity than the input gas stream.

19. The system according to claim 18, wherein the system is configured to produce an output gas stream that comprises a cooler temperature than the input gas stream.

20. The system according to claim 18, further comprising a CPAP device, wherein the input gas stream is configured to be pressurized air supplied by the CPAP device.

21. The system according to claim 18, further comprising an oxygen tank or an oxygen concentrator, wherein the input gas stream is configured to be oxygen supplied by the oxygen tank or the oxygen concentrator.

22. The system according to claim 18, wherein the gas inlet and the gas outlet comprise adaptors for connecting tubing for delivery of the input gas stream or exit of the output gas stream, respectively, wherein the adaptors are retained on the gas inlet and the gas outlet by inner lip seals, and wherein the adaptors each comprise a center post that connects into the gas inlet or the gas outlet and through which the respective gas stream is configured to flow and an outer ring wall configured such that the tubing will not bend the center post when the tubing is connected.

23. The system according to claim 18, further comprising a device that comprises a cooling core, wherein the cooling core comprises a frozen material,
wherein the output gas stream is configured to come in contact with the cooling core such that the output gas stream cools, thereby providing an output gas stream that is a lower temperature than the output gas stream from the system in the absence of the device with the cooling core.

* * * * *